(12) United States Patent
Ha et al.

(10) Patent No.: US 12,090,039 B2
(45) Date of Patent: Sep. 17, 2024

(54) BIOMIMETIC ARTIFICIAL BLADDER AND METHOD FOR CONTROLLING SAME

(71) Applicants: The Catholic University of Korea Industry-Academic Cooperation Foundation, Seoul (KR); University-Industry Foundation, Yonsei University, Seoul (KR); Research Cooperation Foundation of Yeungnam University, Gyeongsan-si (KR)

(72) Inventors: U-Syn Ha, Seoul (KR); Jongbaeg Kim, Goyang-si (KR); Won Gun Koh, Seoul (KR); Jin Ho Kim, Daegu (KR)

(73) Assignees: THE CATHOLIC UNIVERSITY OF KOREA INDUSTRY-ACADEMIC COOPERATION FOUNDATION, Seoul (KR); UNIVERSITY-INDUSTRY FOUNDATION, YONSEI UNIVERSITY, Seoul (KR); RESEARCH COOPERATION FOUNDATION OF YEUNGNAM UNIVERSITY, Gyeongsangbuk-Do (KR)

(*) Notice: Subject to any disclaimer, the term of this patent is extended or adjusted under 35 U.S.C. 154(b) by 908 days.

(21) Appl. No.: 17/262,551

(22) PCT Filed: Jul. 25, 2019

(86) PCT No.: PCT/KR2019/009240
§ 371 (c)(1),
(2) Date: Jan. 22, 2021

(87) PCT Pub. No.: WO2020/022805
PCT Pub. Date: Jan. 30, 2020

(65) Prior Publication Data
US 2021/0353402 A1    Nov. 18, 2021

(30) Foreign Application Priority Data

Jul. 25, 2018    (KR) .................. 10-2018-0086354

(51) Int. Cl.
*A61F 2/04*    (2013.01)
*A61F 2/48*    (2006.01)
*A61F 2/00*    (2006.01)

(52) U.S. Cl.
CPC .............. *A61F 2/042* (2013.01); *A61F 2/482* (2021.08); *A61F 2002/009* (2013.01); *A61F 2250/0013* (2013.01)

(58) Field of Classification Search
CPC ................... A61F 2/0036; A61F 2/042; A61F 2250/0013; A61F 2250/0002; A61M 1/71;
(Continued)

(56) References Cited

U.S. PATENT DOCUMENTS 3,750,194 A * 8/1973 Summers ................ A61F 2/004
128/DIG. 25
3,810,259 A * 5/1974 Summers .............. A61F 2/0036
128/DIG. 25
(Continued)

FOREIGN PATENT DOCUMENTS

JP    2003-522001 A    7/2003
JP    2011-173900 A    9/2011
(Continued)

OTHER PUBLICATIONS

Int'l Search Report and Written Opinion issued Oct. 29, 2019 in Int'l Application No. PCT/KR2019/009240, English translation of Int'l Search Report only.

*Primary Examiner* — Seema Mathew
(74) *Attorney, Agent, or Firm* — Panitch Schwarze Belisario & Nadel LLP

(57) ABSTRACT

An artificial bladder is provided, including: a main body which includes an inlet port, an outlet port, an inner wall that
(Continued)

forms a first reservoir portion configured to store urine between the inlet port and the outlet port and that is expandable and contractible. An outer wall forms a second reservoir portion configured to surround at least a partial region of the inner wall. A sensor is attached to the inner wall, has a surface having a wrinkled structure, and is provided so that, when the volume of the first reservoir portion increases, the wrinkled structure stretches out and resistance of the sensor changes. A control unit is provided to discharge the urine in the first reservoir portion through the outlet port according to a result detected by the sensor.

16 Claims, 8 Drawing Sheets

(58) Field of Classification Search
CPC ........ A61M 2210/1078; A61M 27/002; A61M 2205/3303; A61M 1/73
See application file for complete search history.

(56) References Cited

U.S. PATENT DOCUMENTS

| | | | | | |
|---|---|---|---|---|---|
| 3,863,622 | A | * | 2/1975 | Buuck | A61F 2/004 128/DIG. 25 |
| 3,953,897 | A | * | 5/1976 | Chevallet | A61F 2/042 128/DIG. 21 |
| 3,958,562 | A | * | 5/1976 | Hakim | A61B 5/031 128/DIG. 21 |
| 4,044,401 | A | * | 8/1977 | Guiset | A61F 2/042 623/23.65 |
| 4,228,550 | A | * | 10/1980 | Salkind | A61F 2/042 623/23.66 |
| 4,961,747 | A | * | 10/1990 | Wascher | A61F 2/042 623/23.65 |
| 4,969,474 | A | * | 11/1990 | Schwarz | A61F 2/004 128/885 |
| 4,969,902 | A | * | 11/1990 | Ravo | A61F 2/0009 128/DIG. 25 |
| 4,976,735 | A | * | 12/1990 | Griffith | A61F 2/042 623/23.65 |
| 5,041,136 | A | * | 8/1991 | Wascher | A61F 2/042 623/23.65 |
| 5,108,430 | A | * | 4/1992 | Ravo | A61F 2/04 623/23.68 |
| 5,370,690 | A | * | 12/1994 | Barrett | A61F 2/042 623/23.65 |
| 7,648,455 | B2 | * | 1/2010 | Forsell | A61F 2/0036 600/30 |
| 9,456,915 | B2 | * | 10/2016 | Chen | G08B 21/18 |
| 9,750,591 | B1 | * | 9/2017 | Sultan | A61B 5/03 |
| 11,202,700 | B1 | * | 12/2021 | Pettlon, Sr. | A61B 5/208 |
| 2002/0045868 | A1 | * | 4/2002 | Reever | A61F 2/042 604/327 |
| 2002/0065563 | A1 | * | 5/2002 | Gerlach | A61F 2/042 623/23.65 |
| 2002/0193884 | A1 | * | 12/2002 | Wasserman | A61F 2/042 623/23.65 |
| 2003/0144648 | A1 | * | 7/2003 | Forsell | A61F 2/004 604/246 |
| 2004/0147871 | A1 | * | 7/2004 | Burnett | A61M 39/24 604/9 |
| 2006/0047269 | A1 | * | 3/2006 | Reever | A61M 27/008 604/544 |
| 2006/0100478 | A1 | * | 5/2006 | Connors | A61F 9/00781 600/29 |
| 2006/0105010 | A1 | * | 5/2006 | Rahe | A61L 27/50 424/422 |
| 2011/0004117 | A1 | | 1/2011 | Neville et al. | |
| 2011/0196194 | A1 | * | 8/2011 | Forsell | A61M 1/80 600/31 |
| 2011/0270409 | A1 | * | 11/2011 | Sambusseti | A61F 2/042 623/23.65 |
| 2013/0172664 | A1 | * | 7/2013 | Schmid | A61F 2/042 600/30 |
| 2016/0135942 | A1 | * | 5/2016 | Drager | A61F 2/0036 600/30 |
| 2016/0287373 | A1 | * | 10/2016 | Sambusseti | A61F 2/0077 |
| 2017/0079761 | A1 | * | 3/2017 | Connors | A61B 5/205 |
| 2017/0165047 | A1 | * | 6/2017 | Sambusseti | A61M 25/10 |
| 2017/0216012 | A1 | * | 8/2017 | Sambusseti | A61F 2/042 |
| 2017/0231748 | A1 | * | 8/2017 | Sambusseti | A61F 2/042 623/23.65 |
| 2017/0348507 | A1 | * | 12/2017 | Erbey, II | A61M 25/04 |
| 2018/0104408 | A1 | * | 4/2018 | Li | A61L 31/14 |
| 2018/0193618 | A1 | * | 7/2018 | Erbey, II | A61M 1/74 |
| 2018/0289307 | A1 | * | 10/2018 | Jensen | G01L 19/0023 |
| 2019/0091003 | A1 | * | 3/2019 | Forsell | A61F 2/0036 |
| 2019/0099584 | A1 | * | 4/2019 | Erbey, II | A61M 27/008 |
| 2019/0254804 | A1 | * | 8/2019 | Folan | A61F 2/04 |
| 2019/0388212 | A1 | * | 12/2019 | Ha | A61L 27/48 |
| 2021/0353402 | A1 | * | 11/2021 | Ha | A61M 1/00 |
| 2022/0117716 | A1 | * | 4/2022 | Yachia | A61B 1/00082 |
| 2022/0167921 | A1 | * | 6/2022 | Aljuri | A61B 5/14539 |
| 2022/0203077 | A1 | * | 6/2022 | Folan | A61F 2/04 |
| 2022/0296866 | A1 | * | 9/2022 | Taylor | A61M 31/002 |
| 2023/0200974 | A1 | * | 6/2023 | Kim | G01L 1/144 623/23.65 |
| 2023/0218378 | A1 | * | 7/2023 | Kristensen | A61F 2/0022 600/30 |
| 2023/0293316 | A1 | * | 9/2023 | Watschke | A61F 2/26 600/31 |

FOREIGN PATENT DOCUMENTS

| | | |
|---|---|---|
| JP | 2017-185366 A | 10/2017 |
| KR | 10-2016-0103852 A | 9/2016 |
| WO | 01/58503 A1 | 8/2001 |

* cited by examiner

FIG. 3A
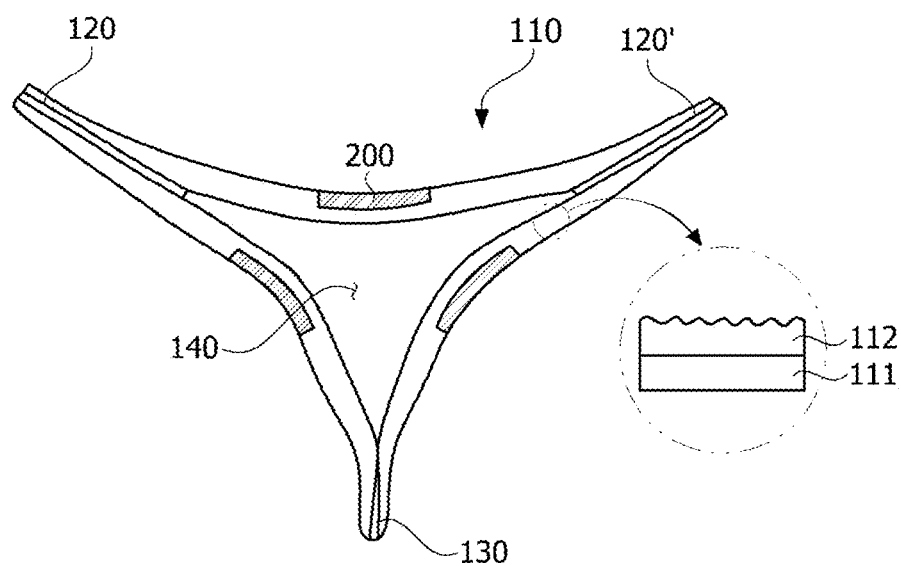
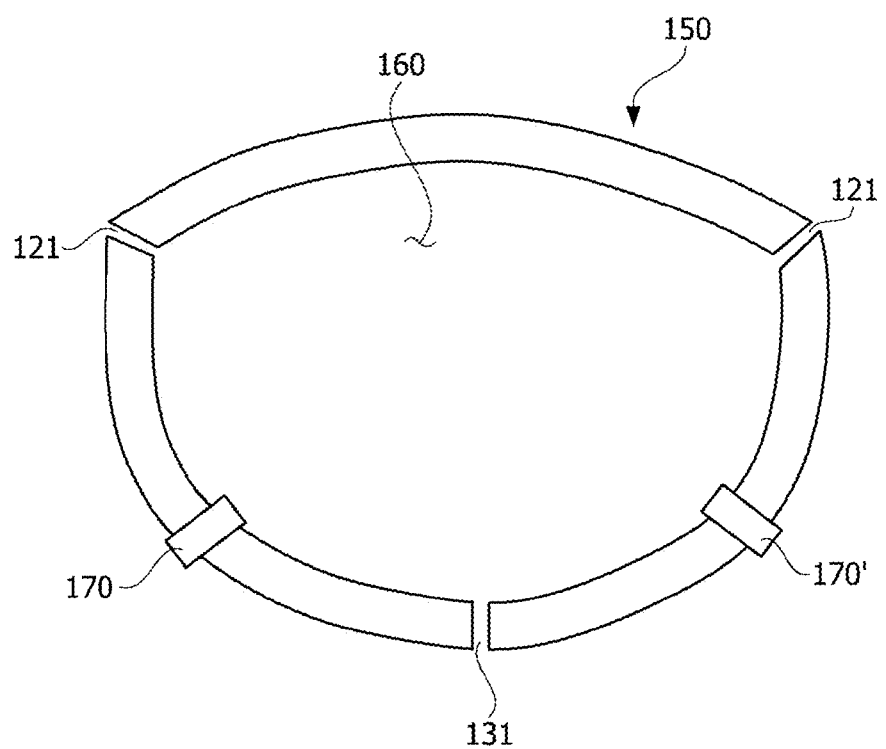
FIG. 3B

FIG. 4A
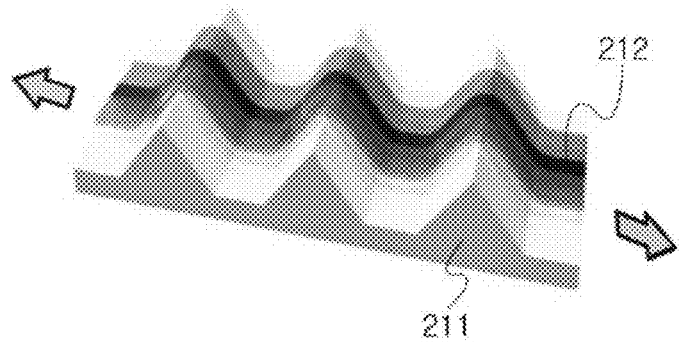
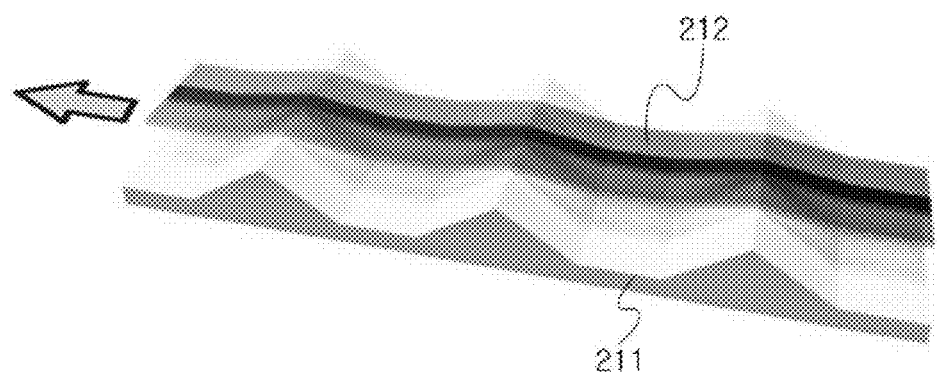
FIG. 4B

FIG. 7A
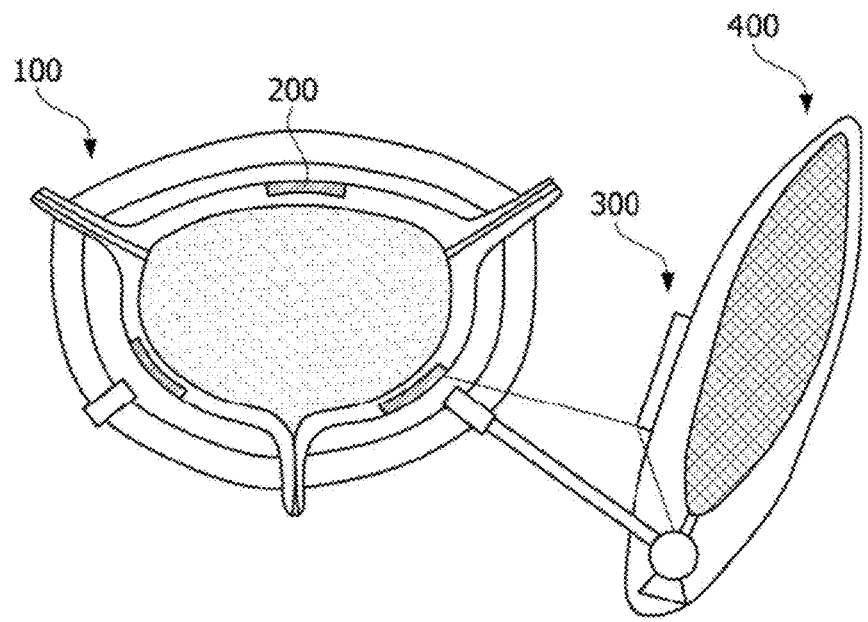
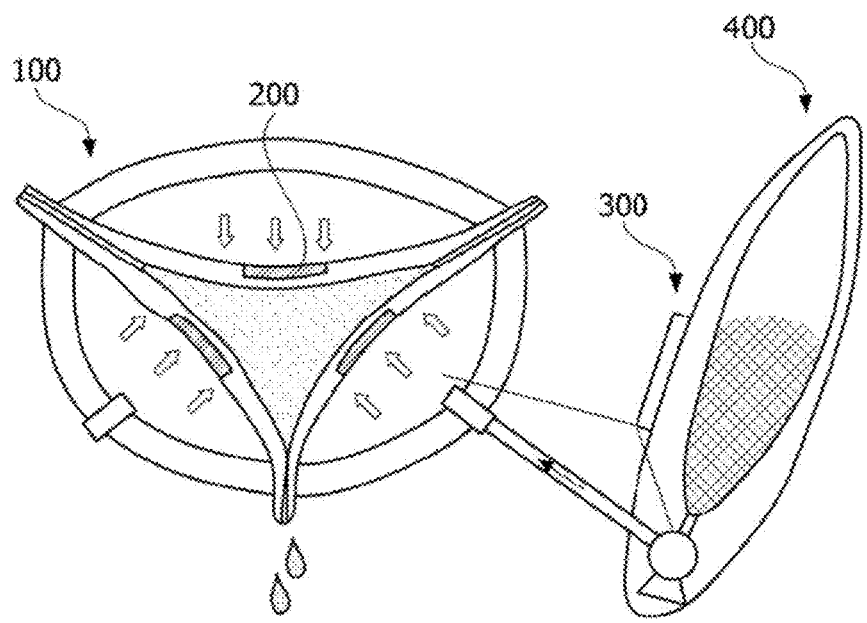
FIG. 7B

FIG. 8A
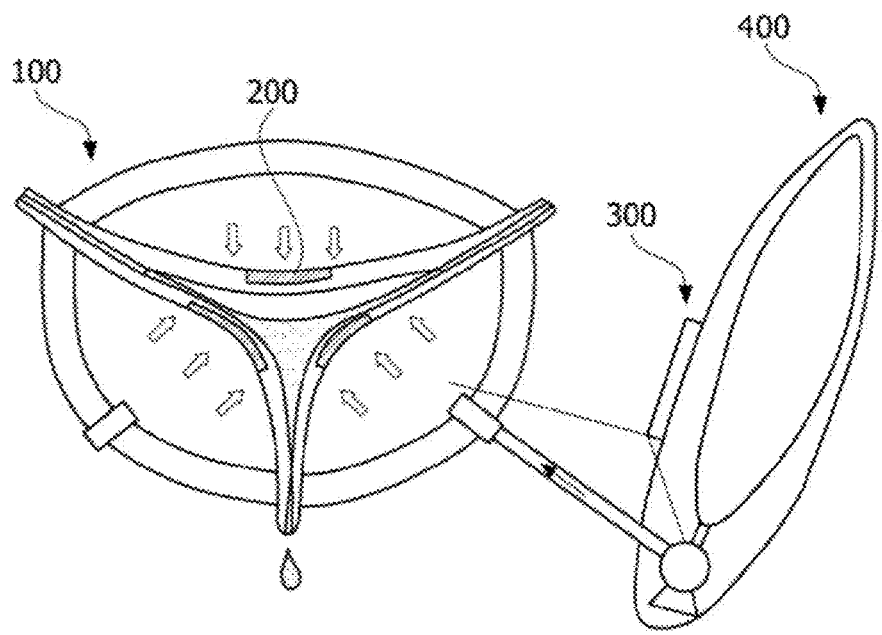
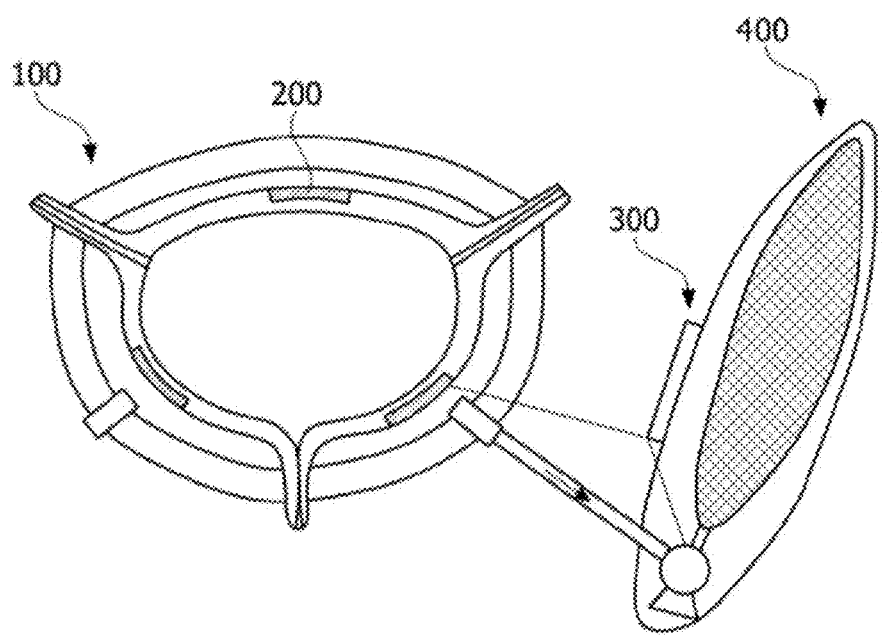
FIG. 8B

BIOMIMETIC ARTIFICIAL BLADDER AND METHOD FOR CONTROLLING SAME

CROSS-REFERENCE TO RELATED APPLICATIONS

This application is a Section 371 of International Application No. PCT/KR2019/009240, filed Jul. 25, 2019, which was published in the Korean language on Jan. 30, 2020 under International Publication No. WO 2020/022805 A1, which claims priority under 35 U.S.C. § 119 to Korean Patent Application No. 10-2018-0086354, filed on Jul. 25, 2018 the disclosures of all of which are incorporated herein by reference.

BACKGROUND OF THE DISCLOSURE

The present disclosure relates to a biomimetic artificial bladder, and more particularly, to a biocompatible artificial bladder capable of replacing the human bladder and a method of controlling the same.

Bladder cancer is the seventh most common cancer among males, the mortality rate of bladder cancer is the ninth highest among mortality rates of all cancers, and the number of bladder cancer patients is increasing by 10% or more every year in South Korea. Surgical treatment is absolutely necessary for the cure of bladder cancer, and cystectomy is performed on one-third of all bladder cancer patients.

Meanwhile, for a patient with a nonfunctioning bladder due to spinal cord injury caused by external injury or due to neuromuscular failure caused by diabetic complications, due to irreversible changes in the muscles and nervous system of the bladder, there is no medication or surgical treatment capable of restoring the function of the bladder, and forced urination using a Foley catheter is the only urination method. Therefore, the patient must take the ureter out of the body and wear a urinary drainage bag.

Existing methods of replacing an injured bladder include urinary diversion and forming a reservoir to store urine using a small intestine.

First, urinary diversion, i.e., a method in which the bladder is removed, the ureter is taken out of the body, and then urine is made to flow into a urinary drainage bag, may cause a change in an appearance of a patient and thus lead to a deterioration in the quality of life in terms of mental health.

Also, the case of forming a reservoir using a small intestine includes a method in which, by causing the small intestine of the patient to have a round shape and forming a reservoir, urine is stored in the body and indirectly induced to rise in the reservoir using abdominal pressure so that the urine is discharged.

However, the small intestine is an organ that performs an absorbing function in terms of physiology, and thus, in the case in which an artificial bladder is formed using the small intestine, a problem may occur due to reabsorption of uremic toxins and electrolytes in urine upon urine storage. In addition, since the small intestine itself is unable to generate contractile force and thus there is no pressure rise in the reservoir, bladder fullness cannot be detected, effective urination is not performed, and thus there is a problem in that complications such as renal function deterioration or infection may occur.

Such limits of the existing bladder replacement techniques may, for bladder cancer patients, cause rejection or delay of bladder ablation during treatment process and deteriorate treatment results and, for patients with a nonfunctioning bladder, cause renal function deterioration and infection due to using a Foley catheter for a long period of time.

Therefore, there is a demand for development of an artificial bladder capable of overcoming such limits of the existing bladder replacement techniques.

BRIEF SUMMARY OF THE DISCLOSURE

The present disclosure provides a biocompatible artificial bladder, which is capable of replacing the human bladder in order to overcome limits of existing bladder replacement techniques, and a method of controlling the same.

One embodiment of the present disclosure provides an artificial bladder including: a main body which includes an inlet port, an outlet port, an inner wall that forms a first reservoir portion configured to store urine between the inlet port and the outlet port and that is provided to be expandable and contractible, and an outer wall that forms a second reservoir portion configured to surround at least a partial region of the inner wall; a sensor which is attached to the inner wall, has a surface having a wrinkled structure, and is provided so that, when a volume of the first reservoir portion increases, the wrinkled structure stretches out and resistance of the sensor changes; and a control unit which is provided to discharge the urine in the first reservoir portion through the outlet port according to a result detected by the sensor.

The outer wall may have a fluid port provided to introduce a fluid into the second reservoir portion or discharge the fluid from the second reservoir portion to the outside.

The artificial bladder may include a fluid storage tank that has a predetermined reservoir, a fluid flow path configured to connect the fluid storage tank and the fluid port, and a pump provided to allow the fluid to flow to the fluid flow path.

The control unit may be provided to operate the pump according to the result detected by the sensor.

The control unit may control the pump to introduce the fluid from the fluid storage tank into the second reservoir portion such that the inner wall contracts.

The control unit may control the pump to introduce the fluid from the second reservoir portion into the fluid storage tank such that the inner wall expands.

The pump may be a two-way pump provided to allow the fluid to flow to any one of the fluid storage tank or the second reservoir portion.

The inner wall may include a first layer that faces the second reservoir portion and a second layer that faces the first reservoir portion.

The first layer may be made of a silicone-based material so as to be expandable and contractible, and the second layer may be formed to include a material for inhibiting calcification.

The outer wall may be formed to include a material for inhibiting fibrosis.

The sensor may include a strain sensor provided to measure a change in the volume of the first reservoir portion.

The strain sensor may be provided so that resistance thereof changes when strain of a predetermined value or more is applied.

The strain sensor may be provided to detect a pre-loading region to which strain of less than the predetermined value is applied and an operating region to which the strain of the predetermined value or more is applied and may be provided to measure an amount of urine stored in the first reservoir portion only in the operating region.

The strain sensor may include an elastic substrate that has a wrinkled structure and a piezoresistor that is formed of a nanomaterial film or a nanomaterial polymer composite.

A method of controlling the artificial bladder according to one embodiment of the present disclosure may include, when the expansion of the inner wall is detected by the sensor, injecting the fluid into the second reservoir portion to discharge urine.

The method may further include, when the discharge of urine is completed, discharging the fluid in the second reservoir portion to the fluid storage tank.

[Advantageous Effects]

An exemplary artificial bladder of the present disclosure can provide, to patients who underwent cystectomy or patients with nonfunctioning bladder, an artificial bladder that is biocompatible and allows active urination.

BRIEF DESCRIPTION OF THE DRAWINGS

The following description of embodiments of the disclosure will be better understood when read in conjunction with the appended drawings. It should be understood, however, that the disclosure is not limited to the precise arrangements and instrumentalities shown. In the drawings:

FIGS. 2, 3A, and 3B are schematic diagrams illustrating a main body according to an embodiment of the present disclosure.

FIGS. 4A and 4B is a schematic diagram illustrating a sensor according to an embodiment of the present disclosure.

FIGS. 7A, 7B, 8A, and 8B are schematic diagrams for describing a method of storing and discharging urine using the artificial bladder according to an embodiment of the present disclosure.

DETAILED DESCRIPTION OF THE DISCLOSURE

Figure 1:
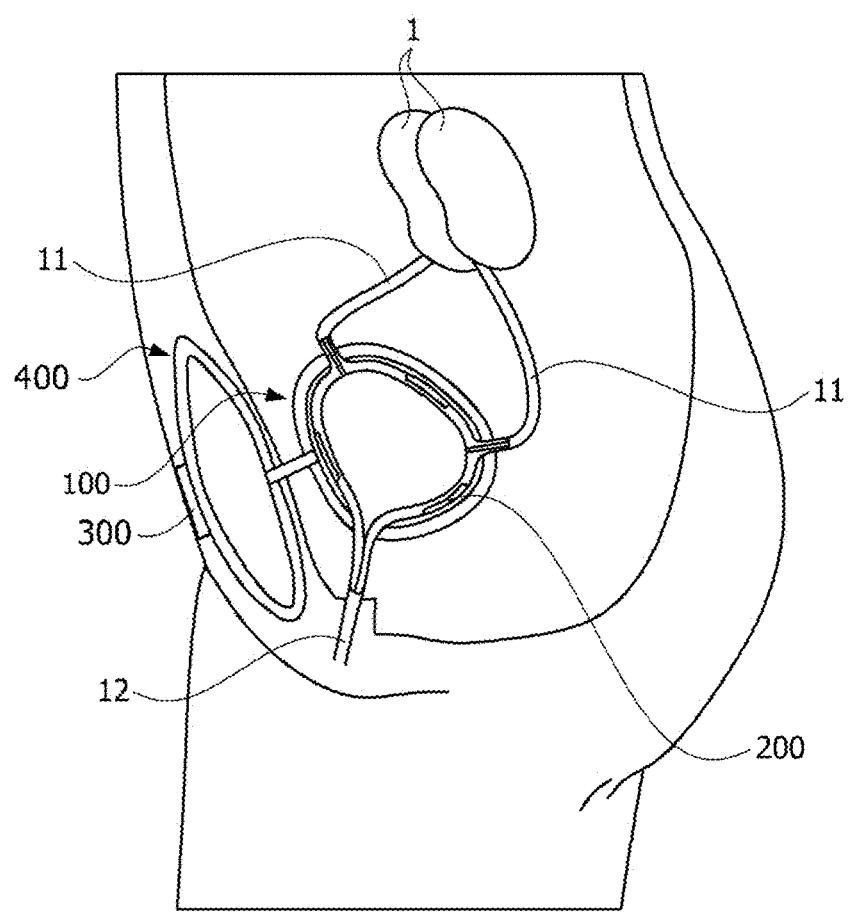
FIG. 1 is a schematic diagram illustrating a state in which an artificial bladder according to an embodiment of the present disclosure is inserted into the body.

Hereinafter, exemplary embodiments of the present disclosure will be described in detail with reference to the accompanying drawings. Terms or words used in this specification and the claims are not to be interpreted as having general or dictionary meanings and should be interpreted as having meanings and concepts which correspond with the technical idea of the present disclosure based on the principle that the inventor can properly define the concept of the terms to describe his or her own invention in the best possible way.

Also, elements which are identical or correspond to each other may be denoted by the same or similar reference numerals throughout the drawings, and repeated description thereof will be omitted. For convenience of description, the size and shape of each illustrated component may have been exaggerated or reduced.

Therefore, embodiments described herein and configurations illustrated in the drawings are merely the most preferred embodiments of the present disclosure and do not represent the entire technical idea of the present disclosure, and thus, it should be understood that various equivalents and modifications, which can replace the most preferred embodiments, may be present at the time of filing this application.

The present disclosure relates to an artificial bladder. According to an exemplary artificial bladder according to the present disclosure, it is possible to provide an artificial bladder that is biocompatible and allows active urination.

Figure 2:
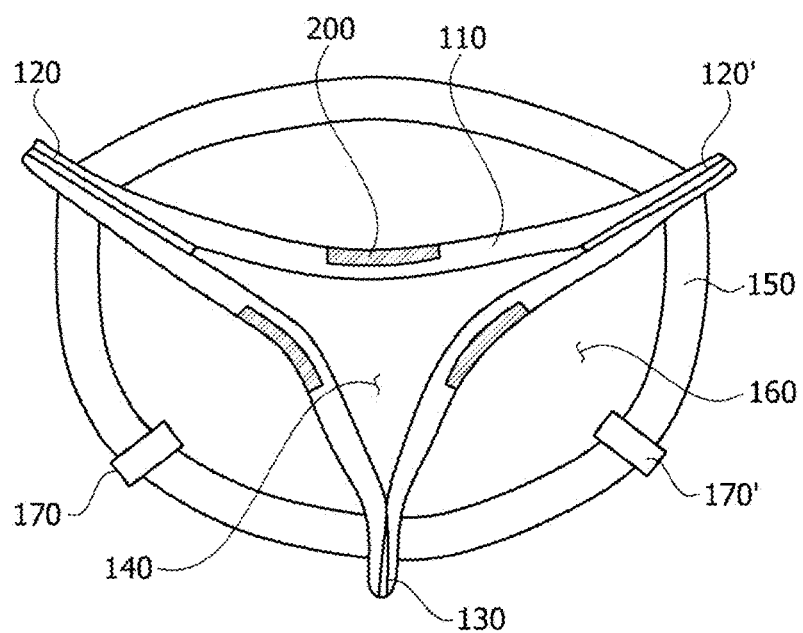

FIG. 1 is a schematic diagram illustrating a state in which an artificial bladder 10 according to an embodiment of the present disclosure is inserted into the human body, and FIGS. 2, 3A, and 3B are schematic diagrams illustrating a main body 100 according to an embodiment of the present disclosure.

Referring to FIGS. 1 to 3B, the artificial bladder 10 of the present disclosure may include the main body 100, a sensor 200, and a control unit 300.

The main body 100 may include an inlet port 120, an outlet port 130, and an inner wall 110 that forms a first reservoir portion 140 configured to store urine between the inlet port 120 and the outlet port 130 and that is provided to be expandable and contractible.

Here, the first reservoir portion 140 may be provided so that the volume of the first reservoir portion 140 changes according to the amount of urine.

Also, the main body 100 may include an outer wall 150 that forms a second reservoir portion 160 configured to surround at least a partial region of the inner wall 110.

In particular, the outer wall 150 forming the second reservoir portion 160 may be provided to surround the first reservoir portion 140, and the outer wall 150 may be provided to support the shape of the second reservoir portion 160.

Also, the sensor 200 may be attached to the inner wall 110, have a surface having a wrinkled structure, and be provided so that, when the volume of the first reservoir portion 140 increases, the wrinkled structure stretches out and resistance of the sensor 200 changes.

Also, the control unit 300 may be provided to discharge the urine in the first reservoir portion 140 through the outlet port 130 according to a result detected by the sensor 200.

More specifically, the inlet port 120 may be an inlet provided to store urine in the first reservoir portion 140, and the outlet port 130 may be an outlet provided to discharge the urine stored in the first reservoir portion 140 to the outside.

The inlet port 120 may be provided as a pair of inlet ports 120 and 120' to be connected to each ureter 11 connected to one of a pair of kidneys 1 in the human body.

That is, for example, the pair of inlet ports 120 and 120' may perform a function of the human ureter.

Also, the outlet port 130 may be provided to be connected to a urethra 12 in the human body, and for example, may perform a function of the human urethra.

The inner wall 110 may be provided to be expandable and contractible so that the volume of the first reservoir portion 140 changes according to the amount of urine introduced through the inlet ports 120 and 120'.

The outer wall 150 may include a fluid port 170 provided to introduce a fluid into the second reservoir portion 160 and discharge the fluid from the second reservoir portion 160 to the outside.

More specifically, the outer wall 150 may include one or more fluid ports 170 and 170' so that the fluid flows into the second reservoir portion 160. For example, based on the outlet port 130, the fluid ports 170 and 170' may be provided at both sides of the outlet port 130, but the present disclosure is not limited thereto.

That is, the pair of fluid ports 170 and 170' may be provided on the outer wall 150, but the present disclosure is not limited thereto.

Also, the outer wall 150 may include first through-holes 121 and 121' through which the inlet ports 120 and 120' respectively pass and a second through-hole 131 through which the outlet port 130 passes.

Consequently, the inlet port 120 provided on the inner wall 110 may pass through the first through-hole 121 to be connected to the human ureter, and the outlet port 130 may pass through the second through-hole 131 to be connected to the human urethra.

Referring to FIGS. 3A and 3B, the inner wall 110 and the outer wall 150 may be made of a biocompatible polymer material.

More specifically, the inner wall 110 may include a first layer 111 that faces the second reservoir portion 160 and a second layer 112 that faces the first reservoir portion 140.

In particular, the second layer 112 may be provided on the first layer 111.

More specifically, the first layer 111 may be made of a silicone-based material so as to be expandable and contractible.

For example, the silicone-based material may be any one of silicone resins made of polydimethylsiloxane (PDMS) and oligosiloxane molecules and synthetic polymers of one or more selected therefrom but is not limited thereto.

Also, the second layer 112 may be formed to include a material for inhibiting calcification.

More specifically, the second layer 112 may include a material for inhibiting calcification to suppress calcification upon contact with urine.

For example, the material for inhibiting calcification may be any one of polyethylene glycol (PEG), polyacrylic acid (PAA), hyaluronic acid (HA), alginate, and natural or synthetic polymer mixtures of one or more selected therefrom but is not limited thereto.

Since urine is oversaturated with calcium, continuous calcification occurs in the second layer 112, which is a contact surface that comes in direct contact with urine.

Therefore, by forming the inner wall 110 so that the second layer includes the material for inhibiting calcification as described above, there is an effect of suppressing calcification and suppressing formation of biofilms (to which bacteria are attached) due to bacterial infection.

For example, a surface of a poly(methylmethacrylate) (PMMA)-based base material layer, e.g., an ocular prosthesis, may be coated with a PEG hydrogel using a grafting-based surface modification technology to coat the surface of the PMMA-based base material layer with a PEG hydrogel thin film and manufacture the inner wall 110.

That is, for example, the inner wall 110 may be manufactured by combining the second layer, in which the PMMA-based base material layer is coated with the PEG hydrogel thin film, with a silicone surface which is the first layer. PEG is widely known to form strong hydrogen bonds with water and prevent non-specific adsorption of other materials on the surface. Therefore, coating with PEG has an effect of suppressing calcification and biofilms. Coating may also be performed with the above-mentioned materials for inhibiting calcification other than PEG.

Also, in still another embodiment, for the inner wall 110, a highly compliant hydrogel material may be synthesized using PEG to form a predetermined base material layer.

The base material layer formed as described above may be directly used as an inner wall material. Here, the PEG hydrogel may be formed as a hydrogel having a double network structure in which PEG and another hydrophilic polymer are combined, but the present disclosure is not limited thereto.

For example, for the PEG hydrogel, a PEG macromer may be exposed to ultraviolet (UV) light to generate the PEG hydrogel, and then the PEG hydrogel may be irradiated with UV light to form a cross-link with another hydrophilic monomer (second monomer) so that an interpenetration hydrogel, i.e., the hydrogel having a double network structure, is manufactured.

In a case in which the inner wall 110 is formed using a predetermined base material layer as above, as described above, the base material layer may be used as a material of the inner wall 110 without the inner wall 110 being divided into a first layer and a second layer.

Meanwhile, the outer wall 150 may be formed to include a material for inhibiting fibrosis.

More specifically, the outer wall 150 may be provided to maintain a predetermined shape of the second reservoir portion 160 and may be formed to include a material for inhibiting fibrosis in order to, upon being inserted into the body, suppress fibrosis of the surrounding organs and tissues in the body.

For example, the material for inhibiting fibrosis may be any one of PEG, PAA, HA, alignate, and mixtures of one or more selected therefrom but is not limited thereto.

The outer wall 150 that comes in direct contact with the inside of the human body may cause an immune-inflammatory response due to foreign substances and thus cause fibrosis.

Therefore, by forming the outer wall 150 to include the material for inhibiting fibrosis as above, there is an effect of suppressing fibrosis.

For example, a base material layer including a silicone-based material may be coated with a polymer thin film, which is formed using a layer-by-layer deposition (LbL deposition)-based surface modification technology, to manufacture the outer wall 150.

More specifically, when a PDMS-based base material layer is alternately dipped in positively-charged and negatively-charged polyelectrolyte aqueous solutions, oppositely-charged layers may be stacked alternately and repeatedly and form a thin film.

Here, a polymer such as PAA, HA, and PEG may be controlled to be stacked on the last layer of the thin film to suppress fibrosis.

The fibrosis occurs due to proteins and cells that take part in inflammatory response, and in the present disclosure, by using the above-described materials, cell adhesion is prevented and generation of various protein factors is reduced to suppress fibrosis.

Here, for example, the silicone-based material may be any one of silicone resins made of PDMS and oligosiloxane molecules and synthetic polymers of one or more selected therefrom but is not limited thereto.

Here, the outer wall 150 may not only be manufactured using the above-described LbL deposition-based surface modification technology but may also be manufactured using the hydrogel grafting-based surface modification method described above with regards to the inner wall 110.

Meanwhile, the second reservoir portion 160 may be defined as a reservoir between the inner wall 110 and the outer wall 150.

In particular, the second reservoir portion 160 may be defined as a reservoir between the second layer 112 of the inner wall 110 and the outer wall 150.

Figure 5:
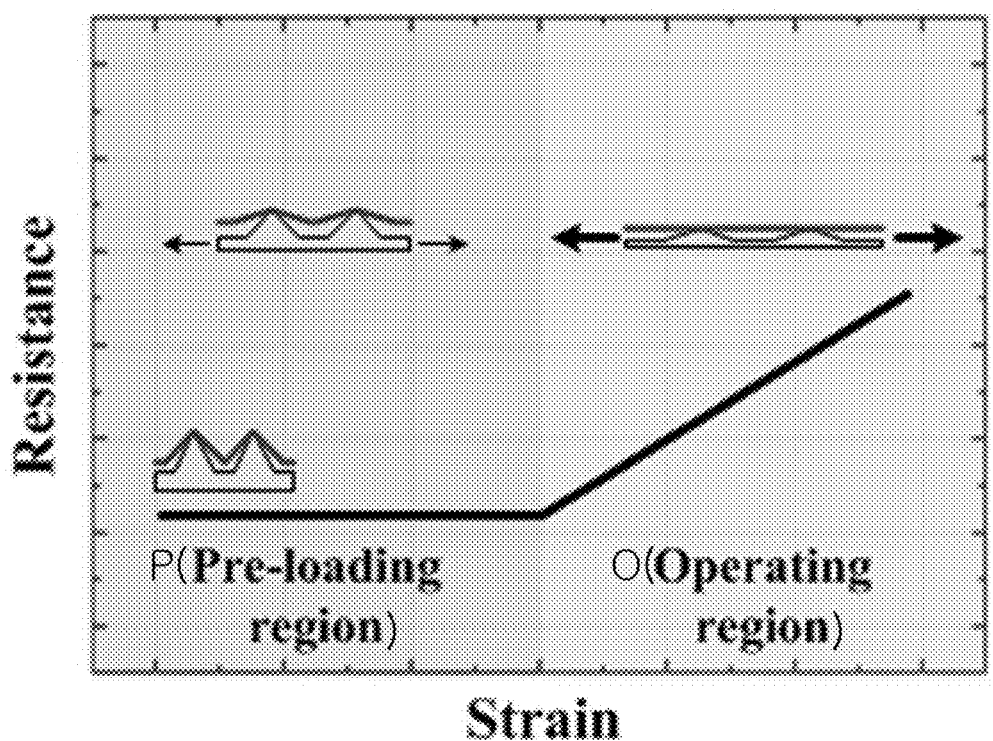
FIG. 5 is a view for describing an operation of the sensor according to an embodiment of the present disclosure.

Meanwhile, FIGS. 4A and 4B are schematic diagrams illustrating the sensor 200 according to an embodiment of the present disclosure, and FIG. 5 is a view for describing an operation of the sensor 200 according to an embodiment of the present disclosure.

Referring to FIGS. 4A and 4B, the sensor 200 may be attached to the inner wall 110 of the main body, have a surface having a wrinkled structure, and be provided so that, when the volume of the first reservoir portion 140 increases, the wrinkled structure stretches out and resistance of the sensor 200 changes.

More specifically, the sensor 200 may be attached to the second layer 112 of the inner wall 110.

Here, one or more sensors 200 may be attached to the inner wall 110, and for example, three sensors 200 may be attached as illustrated in the drawing, but the present disclosure is not limited thereto.

Also, the sensor 200 may be a strain sensor 210 configured to measure expansion and a volume change of the inner wall 110.

The strain sensor 210 may include a piezoresistor 212 that is made of a nanomaterial film or a nanomaterial polymer composite and an elastic substrate 211 that has a wrinkled structure.

In particular, the strain sensor 210 may have a form in which the piezoresistor 212 is placed on the elastic substrate 211 having the wrinkled structure.

For example, the elastic substrate 211 may be manufactured using an elastic material such as PDMS and Ecoflex.

Also, a carbon nanomaterial, a nanomaterial film, or a nanomaterial polymer composite may be used to manufacture the piezoresistor 212 so that the piezoresistor 212 has high sensitivity to detect even slight vibrations.

For example, the nanomaterial film may include a carbon nanotube, graphene, a nanowire, and nanoparticles, but the present disclosure is not limited thereto.

Also, the nanomaterial polymer composite may be any one or more selected from combinations of polymers such as PDMS and polyurethane (PU) and the above-mentioned nanomaterials, but the present disclosure is not limited thereto.

A partial region of one surface of the elastic substrate 211 may be coated with the piezoresistor 212 to manufacture the strain sensor 210.

Meanwhile, the strain sensor 210 manufactured as described above may be provided to be attached to the inner wall 110 so that, when the volume of the first reservoir portion 140 increases, the elastic substrate 211 having the wrinkled structure, which has the piezoresistor 212 placed thereon, stretches out and resistance of the strain sensor 210 changes.

In particular, the strain sensor 210 may be provided so that the resistance thereof changes when strain of a predetermined value or more is applied.

More specifically, referring to FIG. 5, the strain sensor 210 may be provided to detect a pre-loading region P to which strain of less than the predetermined value is applied and an operating region O to which the strain of the predetermined value or more is applied and may be provided to measure an amount of urine stored in the first reservoir portion 140 only in the operating region.

In the pre-loading region P, which is a region irrelevant to whether urine is discharged, the elastic substrate 211 having the wrinkled structure stretches out, but strain is not applied to the piezoresistor 212.

On the other hand, in the operating region O, strain begins to be applied to the piezoresistor 212 simultaneously as the elastic substrate 211 having the wrinkled structure stretches out such that the amount of urine stored in the first reservoir portion 140 may be measured from a change in resistance according to the applied strain, and a timing of urination may be determined.

For example, in a case in which the maximum capacity of the first reservoir portion 140 is 400 ml, the amount of urine stored in the first reservoir portion 140 may be in a range of 0 ml to less than 100 ml in the pre-loading region P and may be in a range of 100 ml to 400 ml in the operating region O.

In particular, the sensor may be provided to, when the amount of urine stored in the first reservoir portion 140 is in a range of 300 ml to 400 ml, determine that a timing of urination is reached and discharge urine to the outside.

More specifically, the sensor may not operate in the pre-loading region P, in which the amount of urine stored in the first reservoir portion 140 is in the range of 0 ml to less than 100 ml, because the pre-loading region P is irrelevant to whether urine is discharged and thus precise measurement of the amount of urine is not necessary therein, and the sensor may precisely measure the amount of urine to determine a timing of urination in the operating region O in which the amount of urine stored in the first reservoir portion 140 is in the range of 100 ml to 400 ml.

Therefore, by manufacturing the sensor 200, which is configured as described above, with a flexible material having a wrinkled structure, the amount of urine in the first reservoir portion (bladder) may be stably measured to detect a timing of urination, and the control unit 300, which will be described below, may allow urine to be discharged according to the detected result.

Meanwhile, the artificial bladder 10 according to an embodiment of the present disclosure further includes the control unit 300 and a fluid supply unit 400.

Figure 6:
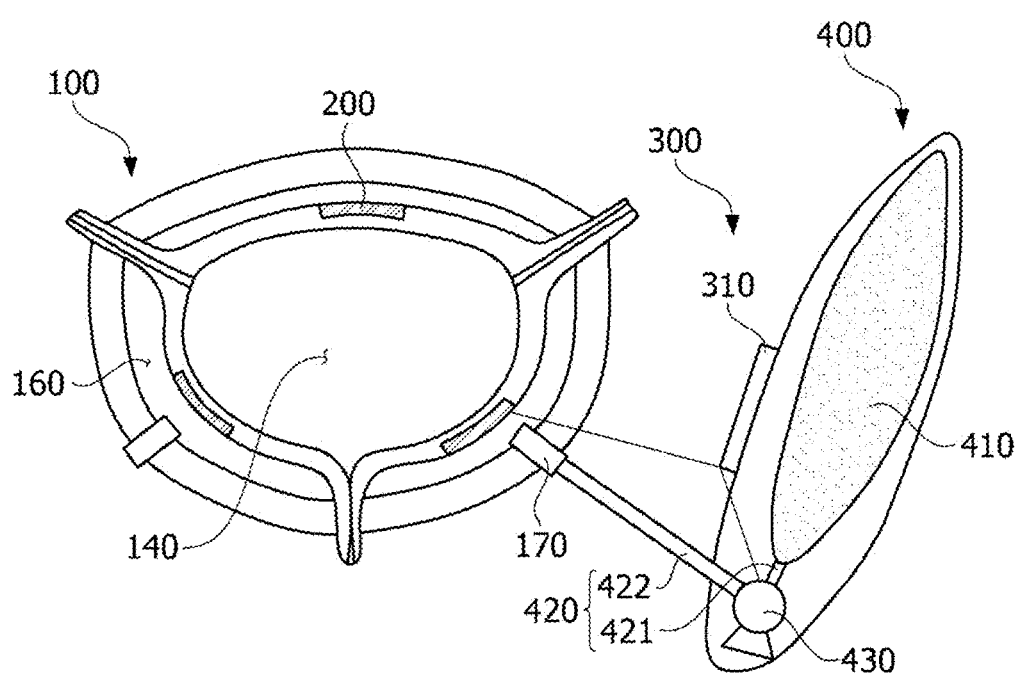
FIG. 6 is a schematic diagram illustrating a control unit and a fluid supply unit according to an embodiment of the present disclosure.

FIG. 6 is a schematic diagram illustrating the control unit 300 and the fluid supply unit 400 according to an embodiment of the present disclosure.

Referring to FIG. 6, the control unit 300 may be provided to operate a pump 430 according to a result detected by the sensor 200.

Also, the control unit 300 may control the pump 430 to introduce a fluid from a fluid storage tank 410 to the second reservoir portion 160 such that the inner wall 110 contracts.

Also, the control unit 300 may control the pump 430 to introduce the fluid from the second reservoir portion 160 to the fluid storage tank 410 such that the inner wall 110 expands.

More specifically, the control unit 300 may include a controller 310 configured to operate the pump 430 according to a result detected by the sensor 200.

In addition, the fluid supply unit 400 of the present disclosure includes the fluid storage tank 410 that has a predetermined reservoir, a fluid flow path 420 configured to connect the fluid storage tank 410 and the fluid port 170, and the pump 430 provided to cause the fluid to flow to the fluid flow path 420.

Here, the pump 430 may be operated by the controller 310 according to a result detected by the sensor 200.

Here, the fluid may be water but is not limited thereto.

A fluid, e.g., water, may be stored in the fluid storage tank 410.

Also, the fluid flow path 420 may include a first flow path 421 and a second flow path 422 to connect the fluid storage tank 410 and the fluid port 170.

More specifically, the first flow path 421 may be connected so that a fluid is movable between the fluid storage tank 410 and the pump 430, and the second flow path 422 may be connected so that a fluid is movable between the fluid port 170 and the pump 430.

Therefore, the pump 430 may be provided to allow the fluid to flow to the first and second flow paths 421 and 422.

The pump 430 may be provided so that the fluid stored in the fluid storage tank 410 sequentially passes through the first flow path 421 and the second flow path 422 and flows into the second reservoir portion 160.

Also, the pump 430 may be provided so that the fluid stored in the second reservoir portion 160 sequentially passes through the second flow path 422 and the first flow path 421 and flows into the fluid storage tank 410.

In addition, the control unit 300 may further include a charger (not illustrated) provided to supply power to the controller 310 and the pump 430, and the charger may be a wireless charger that allows wireless charging.

Also, in order to receive a result detected by the sensor 200, which is attached to the inner wall 110, and operate the pump 430 on the basis of the detected result, the controller 310 may be electrically connected to each of the sensor 200 and the pump 430.

That is, the controller 310 may be interconnected to the sensor 200 and the pump 430, and through the controller 310, the amount of urine stored in the first reservoir portion 140 may be precisely monitored in real time, and urine may be controlled to be discharged according to active determination on a timing of urination.

For example, on the basis of a predetermined value for determining a timing of urination that is pre-input to the controller 310, when the sensor 200 detects that the amount of urine stored in the first reservoir portion 140 is a predetermined value or more, the controller 310 may operate the pump 430 according to the detected result so that the urine inside the first reservoir portion 140 is discharged through the outlet port 130.

For example, the predetermined value may indicate the amount of urine in the first reservoir portion 140 and may be 250 ml or more or 300 ml or more but is not limited thereto.

Also, the pump 430 may be a two-way pump provided to allow the fluid to flow into any one of the fluid storage tank 410 and the second reservoir portion 160.

Therefore, the two-way pump may allow the fluid to flow in a first direction or a second direction according to a signal transmitted from the controller 310.

Here, the first direction indicates a direction in which the fluid flows from the fluid storage tank 410 to the second reservoir portion 160, and the second direction indicates a direction in which the fluid flows from the second reservoir portion 160 to the fluid storage tank 410.

Also, the controller 310 may control the pump to introduce the fluid from the fluid storage tank 410 to the second reservoir portion 160 such that the inner wall 110 contracts.

That is, the controller 310 may control the pump 430 to allow the fluid to flow from the fluid storage tank 410 to the second reservoir portion 160 and control the urine stored in the first reservoir portion 140 to be discharged through the outlet port 130 as a pressure is applied to the inner wall 110 and the inner wall 110 contracts due to the flowing fluid and thus the volume of the first reservoir portion 140 decreases.

In other words, the controller 310 may be provided to control the pump 430 to allow the fluid to flow in the first direction so that, as the inner wall contracts due to the flowing fluid (fluid pressure) and thus the volume of the first reservoir portion 140 decreases, the urine stored in the first reservoir portion 140 is discharged through the outlet port 130.

More specifically, in a case in which, as the amount of stored urine increases and the inner wall 110 gradually expands, the sensor 200 detects that the measured amount of urine in the first reservoir portion 140 is in the range that indicates that a timing of urination is reached, the sensor 200 may transmit a detected signal to the controller 310 electrically connected to the sensor 200, and the controller 310 that receives the signal may operate the pump 430, which is electrically connected to the controller, according to the detected result.

Therefore, as the operated pump 430 allows the fluid to flow from the fluid storage tank 410 to the second reservoir portion 160, a pressure is applied to the inner wall 110 due to the fluid, and thus the inner wall 110 contracts, the volume of the first reservoir portion 140 may decrease, and the urine stored in the first reservoir portion 140 may be discharged through the outlet 130.

In addition, the controller 310 may control the pump 430 to introduce the fluid from the second reservoir portion 160 into the fluid storage tank 410 such that the inner wall 110 expands.

In a case in which the urine stored in the first reservoir portion 140 is discharged, the controller 310 may control the pump 430 to allow the fluid flowing in the second reservoir portion 160 to flow into the fluid storage tank 410 so that the pressure applied to the inner wall 110 is released and the inner wall 110 expands again.

That is, the controller 310 may be provided to control the pump 430 to allow the fluid to flow in the second direction so that, as the inner wall 110 from which a fluid pressure is released expands causing the volume of the first reservoir portion 140 to increase, urine is stored in the first reservoir portion 140 again.

More specifically, when discharge of the urine stored in the first reservoir portion 140 is completed, the sensor 200 may transmit a detected signal to the controller 310 electrically connected to the sensor 200, and the controller 310 that receives the signal may operate the pump 430, which is electrically connected to the controller 310, according to the detected result.

Therefore, as the operated pump 430 allows the fluid flowing in the second reservoir portion 160 to flow into the fluid storage tank 410 such that the pressure applied to the inner wall 110 is released and the inner wall 110 expands again, urine may be stored in the first reservoir portion 140.

The control unit 300 and the fluid supply unit 400 may be inserted into the human body like the above-described main body 100, and thus, the control unit and the fluid supply unit may be made of the same biocompatible material as the above-described outer wall 150.

In particular, the control unit 300 and the fluid supply unit 400 may be disposed to be inserted into subcutaneous fat of the human body.

The present disclosure also provides a method of storing and discharging urine using the above-described artificial bladder 10.

Therefore, the above description of the artificial bladder 10 may identically apply to the method of storing and discharging urine that will be described below.

An exemplary method of controlling the artificial bladder 10 according to an embodiment of the present disclosure is an artificial bladder control method using the above-described artificial bladder 10.

More specifically, the artificial bladder control method may include, when the expansion of the inner wall 110 is detected by the sensor 200, injecting a fluid into the second reservoir portion 160 to discharge urine.

In addition, the artificial bladder control method may include, when the discharge of urine is completed, discharging the fluid in the second reservoir portion 160 to the fluid storage tank 410.

That is, when urine is stored in the first reservoir portion 140, the inner wall 110 expands due to the stored urine, the sensor 200 operates due to the expanded inner wall 110, and the control unit may operate according to a result detected by the sensor 200 and discharge urine.

Here, the sensor 200 may operate only when the amount of urine stored in the first reservoir portion 140 is a predetermined amount or more.

More specifically, the artificial bladder control method may further include, when the inner wall 110 expands and the sensor 200 detects that a timing of urination is reached, operating the pump 430 by the controller 310 to allow the fluid to flow from the fluid storage tank 410 to the second reservoir portion 160.

Consequently, the artificial bladder control method may further include, as a pressure is applied to the inner wall 110 due to the fluid flowing to the second reservoir portion 160 and thus the first reservoir portion 140 contracts, discharging urine.

Also, the artificial bladder control method may further include, after the discharge of urine is completed, operating the pump 430 by the controller 310 to allow the fluid to flow from the second reservoir portion 160 to the fluid storage tank 410.

Consequently, the artificial bladder control method may further include allowing the pressure applied to the inner wall 110 to be released by the fluid flowing to the fluid storage tank 410 such that the first reservoir portion 140 expands.

FIGS. 7A, 7B, 8A and 8B are schematic diagrams for describing a method of storing and discharging urine using the artificial bladder 10 inserted into the body according to an embodiment of the present disclosure.

Hereinafter, the artificial bladder control method using the artificial bladder 10 will be described in more detail with reference to FIGS. 7A, 7B, 8A, and 8B.

First, upon insertion of the above-described artificial bladder 10 into the body, the inlet port 120 and the outlet port 130 of the artificial bladder 10 may be respectively connected to the ureter and urethra in the body.

Urine that passes through the inlet port 120 along the ureter is stored in the first reservoir portion 140 of the artificial bladder 10 inserted into the body.

As the amount of urine stored in the first reservoir portion 140 increases, the inner wall 110 expands.

As illustrated in FIG. 7A, the sensor 200 attached to the inner wall 110 detects the amount of urine stored in the first reservoir portion 140 in the operating region O to which strain of a predetermined value or more is applied.

The control unit operates according to a result detected as above and allows urine to be discharged.

That is, in a case in which the result detected according to the amount of urine detected by the sensor as above indicates that a timing of urination is reached, as illustrated in FIGS. 7B and 8A, the detected signal (detected result) of the sensor is transmitted to the controller, and according to the transmitted detected signal (detected result), the controller controls the pump 430 to be operated to allow the fluid stored in the fluid storage tank 410 to flow into the second reservoir portion 160.

Specifically, by the pump 430 being operated as above, the fluid passes through the first flow path 421 from the fluid storage tank 410, flows to the second flow path 422 via the pump, and then is introduced into the second reservoir portion 160 through the fluid port 170.

Due to the fluid introduced into the second reservoir portion 160 as above, a pressure is applied to the inner wall 110, the first reservoir portion 140 contracts, and thus urine therein passes through the outlet port 130 and is discharged to the outside along the urethra connected to the outlet port 130.

When the discharge of urine is completed, the detected signal (detected result) of the sensor is transmitted to the controller, and according to the transmitted detected signal (detected result), the controller controls the pump 430 to be operated to allow the fluid stored in the second reservoir portion 160 to flow into the fluid storage tank 410.

As illustrated in FIG. 8B, due to the fluid flowing into the fluid storage tank 410, the pressure applied to the inner wall 110 is released, and the first reservoir portion 140 expands again.

As described above, urine is stored in the re-expanded first reservoir portion 140, and the above-described operations are repeated. In this way, the artificial bladder 10 may continuously serve as the human bladder.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. An artificial bladder comprising:
   a main body which includes an inlet port, an outlet port, an inner wall that forms a first reservoir portion configured to store urine between the inlet port and the outlet port and that is provided to be expandable and contractible, and an outer wall that forms a second reservoir portion configured to surround at least a partial region of the inner wall, the outer wall having a fluid port provided to introduce a fluid into the second reservoir portion or discharge the fluid from the second reservoir portion to the outside;
   a sensor which is attached to the inner wall, has a surface having a wrinkled structure, and is provided so that, when a volume of the first reservoir portion increases, the wrinkled structure stretches out and resistance of the sensor changes;
   a control unit which is provided to discharge the urine in the first reservoir portion through the outlet port according to a result detected by the sensor;
   a fluid storage tank having a predetermined reservoir;
   a fluid flow path configured to connect the fluid storage tank and the fluid port; and
   a pump provided to allow the fluid to flow to the fluid flow path.

2. The artificial bladder of claim 1, wherein the control unit is provided to operate the pump according to a result detected by the sensor.

3. The artificial bladder of claim 2, wherein the control unit controls the pump to introduce the fluid from the fluid storage tank into the second reservoir portion such that the inner wall contracts.

4. The artificial bladder of claim 2, wherein the control unit controls the pump to introduce the fluid from the second reservoir portion into the fluid storage tank such that the inner wall expands.

5. The artificial bladder of claim 1, wherein the pump is a two-way pump provided to allow the fluid to flow to any one of the fluid storage tank or the second reservoir portion.

6. The artificial bladder of claim 1, wherein the inner wall includes a first layer that faces the second reservoir portion and a second layer that faces the first reservoir portion.

7. The artificial bladder of claim 6, wherein the first layer is made of a silicone-based material so as to be expandable and contractible, and the second layer is formed to include material for inhibiting calcification.

8. The artificial bladder of claim 1, wherein the outer wall is formed to include a material for inhibiting fibrosis.

9. The artificial bladder of claim 1, wherein the sensor includes a strain sensor provided to measure a change in the volume of the first reservoir portion.

10. The artificial bladder of claim 9, wherein the strain sensor is provided so that resistance thereof changes when strain of a predetermined value or more is applied.

11. The artificial bladder of claim 10, wherein:
the strain sensor is provided to detect a pre-loading region to which strain of less than the predetermined value is applied and an operating region to which the strain of the predetermined value or more is applied; and
the strain sensor is provided to measure an amount of urine stored in the first reservoir portion only in the operating region.

12. The artificial bladder of claim 9, wherein the strain sensor includes an elastic substrate that has a wrinkled structure and a piezoresistor that is formed of a nanomaterial film or a nanomaterial polymer composite.

13. A method of controlling the artificial bladder of claim 1, the method comprising:
detecting the expansion of the inner wall via the sensor, and, subsequently
injecting the fluid into the second reservoir portion to discharge urine.

14. The method of claim 13, further comprising:
discharging the fluid in the second reservoir portion to the fluid storage tank when the discharge of urine is completed.

15. An artificial bladder comprising:
a main body which includes an inlet port, an outlet port, an inner wall that forms a first reservoir portion configured to store urine between the inlet port and the outlet port and that is provided to be expandable and contractible, and an outer wall that forms a second reservoir portion configured to surround at least a partial region of the inner wall, the inner wall including a first layer facing the second reservoir portion and a second layer facing the first reservoir portion, wherein the first layer is made of a silicone-based material so as to be expandable and contractible, and the second layer is formed to include material for inhibiting calcification;
a sensor which is attached to the inner wall, has a surface having a wrinkled structure, and is provided so that, when a volume of the first reservoir portion increases, the wrinkled structure stretches out and resistance of the sensor changes; and
a control unit which is provided to discharge the urine in the first reservoir portion through the outlet port according to a result detected by the sensor.

16. An artificial bladder comprising:
a main body which includes an inlet port, an outlet port, an inner wall that forms a first reservoir portion configured to store urine between the inlet port and the outlet port and that is provided to be expandable and contractible, and an outer wall that forms a second reservoir portion configured to surround at least a partial region of the inner wall;
a sensor which is attached to the inner wall, has a surface having a wrinkled structure, and is provided so that, when a volume of the first reservoir portion increases, the wrinkled structure stretches out and resistance of the sensor changes, the sensor including a strain sensor provided to measure a change in the volume of the first reservoir portion, wherein the strain sensor includes an elastic substrate that has a wrinkled structure and a piezoresistor that is formed of a nanomaterial film or a nanomaterial polymer composite; and
a control unit which is provided to discharge the urine in the first reservoir portion through the outlet port according to a result detected by the sensor.

* * * * *